United States Patent [19]

Lee

[11] 4,342,341

[45] Aug. 3, 1982

[54] BLOOD TRANSFER DEVICE

[75] Inventor: Peter F. Lee, Minneapolis, Minn.

[73] Assignee: Southland Instruments, Inc., Houston, Tex.

[21] Appl. No.: 158,772

[22] Filed: Jun. 12, 1980

Related U.S. Application Data

[63] Continuation-in-part of Ser. No. 13,078, Feb. 21, 1979, Pat. No. 4,274,453.

[51] Int. Cl.³ .............................. B65B 3/04; B67C 7/00
[52] U.S. Cl. ........................................ 141/1; 134/170; 141/90; 141/284; 141/285; 141/330; 222/148
[58] Field of Search ....................... 73/864.16, 864.24; 141/1, 89, 90, 91, 130, 284, 285, 329; 222/83, 85, 88, 148; 134/104, 170, 166 R

[56] References Cited

U.S. PATENT DOCUMENTS

| | | | |
|---|---|---|---|
| 578,944 | 3/1897 | Platz et al. ....................... | 141/329 X |
| 2,193,050 | 3/1940 | Chapman ............................ | 141/329 |
| 2,415,419 | 2/1947 | Cozzoli ............................. | 141/329 |
| 2,541,272 | 2/1951 | Murphy ........................... | 141/329 X |
| 3,294,264 | 12/1966 | Everington ....................... | 222/85 X |
| 3,383,923 | 5/1968 | Conche et al. ..................... | 73/864.31 |
| 3,572,998 | 3/1971 | Anthon ........................... | 222/148 |
| 3,863,507 | 2/1975 | Jones et al. ....................... | 73/864.24 |
| 4,041,994 | 8/1977 | Horwitz et al. ..................... | 141/329 |
| 4,096,893 | 6/1978 | Harvey, Jr. et aL. .......... | 141/329 X |
| 4,170,798 | 10/1979 | Krumdieck ......................... | 141/329 |
| 4,262,711 | 4/1981 | Anderson ....................... | 141/329 X |

OTHER PUBLICATIONS

"Coulter Counter Model 'S'" SR Coulter Electronics, 1964, Hialeah, Fla.

Primary Examiner—Frederick R. Schmidt
Attorney, Agent, or Firm—Merchant, Gould, Smith, Edell, Welter & Schmidt

[57] ABSTRACT

An arrangement for sampling a liquid by a closed procedure which includes penetrating the closure (34) of a container (33) of liquid by a needle (62) having a bore (68), a solid point (63), and a radial passage (66) near the point of communication with the bore, the needle including a space (67) extending coaxially therein in addition to the bore, and outward apertures (70) and (71) communicating with the space and positioned so that when the needle penetrates the closure into the container for a predetermined distance, one of the apertures is within the container and another of the apertures is outside the container.

4 Claims, 12 Drawing Figures

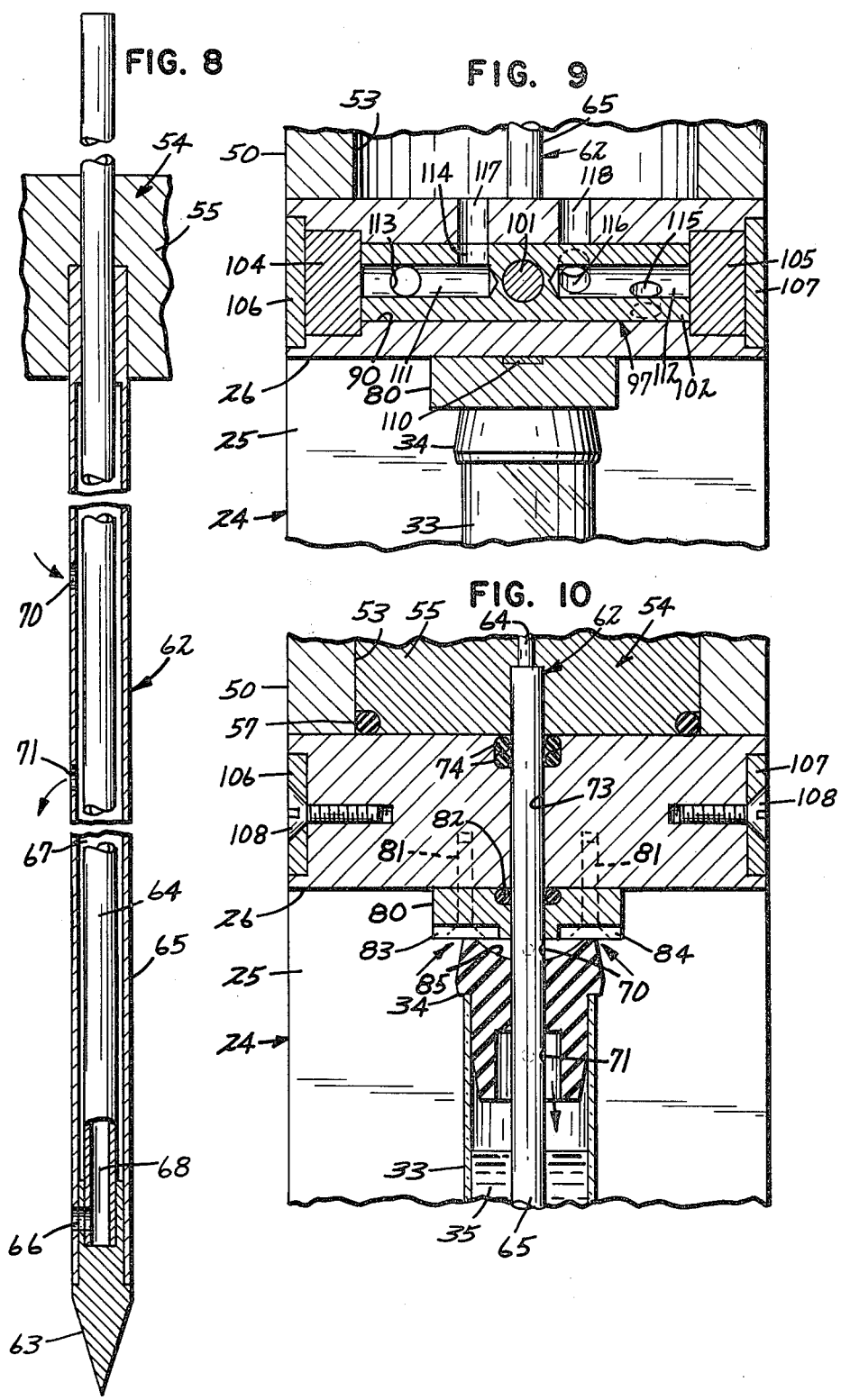

BLOOD TRANSFER DEVICE

This is a continuation-in-part application of my co-pending patent application filed Feb. 21, 1979, Ser. No. 13,078, which issued as U.S. Pat. No. 4,274,453 on June 23, 1981.

TECHNICAL FIELD

This invention relates to the field of medical technology, and specifically to apparatus and procedures for minimizing the occupational hazards of workers who perform routine blood testing using advanced technology.

BACKGROUND OF THE INVENTION

As pointed out in the previous application, one of the great advances in medical technology in recent years is the development of automated equipment for performing comprehensive analyses of blood samples, to give readings of factors identified as red cell count, white cell count, hemoglobin, hematocrit, mean cell volume, mean cell hemoglobin, and mean cell hemoglobin concentration. An automated hematology analyzer aspirates a specimen of blood from a sample container, performs the required tests, prints out the test results, and prepares the equipment for the next specimen, in a time interval less than one minute.

Samples of patients' blood are provided in standard sample containers having rubber stopper closures. Specimen input to the analyzer is both "open" and manual, that is, a technician must take a previously shaken sample container (or must shake the container a predetermined amount), open the container by removing the stopper, immerse the aspirator tip of the analyzer into the sample, and actuate the analyzer. After the specimen input has been completed, the container must be restoppered and disposed of, and any liquid adhering to the outside of the aspirator tip must be removed.

Because the sample container must be opened and manually introduced into the system, laboratory personnel is exposed to a potentially dangerous environment.

All laboratory specimens are regarded as hazardous. Pathogenic microorganisms are readily spread to laboratory personnel by direct contact. With blood samples there is particular concern over exposure to serum hepatitis. The open input of blood specimens to automated systems as described above results in exposure of technicians to contact with the blood dripping from the aspirator tip of the equipment, as well as the residual blood in the container and on the rubber stopper.

My copending application referred to above covers an arrangement for a "closed" specimen input to the analyzer, by enabling transfer of blood from a closed container to the analyzer without exposing the technician to contact with the blood before or after aspiration. The unopened container is secured in a suitable holder: when a manual control is operated a compound transfer needle, connected by an aspiration tube to the analyzer, is forced to enter the container by penetrating the stopper. After aspiration of the sample, the needle is raised out of the container, the stopper material acting to wipe away any liquid adhering to the external surface of the needle, and then to reseal the container. The result is an improved method in which the technician is never exposed to contact with blood at any time.

Refinements in the field of hematology analyzers have resulted in the opportunity for improving the structure described in the previous application. Sources of positive and negative fluid pressure are now available: the analyzer also now includes an automatic procedure for rinsing a sampling needle after each sample is taken, so provision must be made for suitably disposing of the rinsing fluid.

SUMMARY OF THE INVENTION

The present invention still provides a "closed" specimen input to the analyzer, by enabling transfer of blood from an unopened container to the analyzer without exposing the technician to contact with the blood before or after the aspiration of the sample. The stoppered container is secured in a suitable holder: when a first manual control is operated a transfer needle connected to the analyzer by a flexible tube is forced by a fluid motor to penetrate the stopper and enter the container. The analyzer is actuated to aspirate a sample from the container, the needle construction allowing replacement air to enter the container. After the sample is taken the first control is reversely actuated to cause the fluid motor to withdraw the needle from the container, the outer surface of the needle being wiped clean by contact with the closure, which is self-sealing. The analyzer now directs a cleaning liquid into and through the needle, the spent liquid being conducted to a suitable discharge, and the container, still closed, is removed and replaced by another for repetition of the sampling procedure. The result, as before, is an input method in which the technician is never exposed to contact with blood at any time, but it also provides for fluidic rather than human movement of the needle, and for cleansing the needle and discharge of the cleansing fluid.

Various advantages and features of novelty which characterize the invention are pointed out with particularity in the claims annexed hereto and forming a part hereof. However, for a better understanding of the invention, its advantages, and objects attained by its use, reference should be had to the drawing which forms a further part hereof, and to the accompanying descriptive matter, in which there is illustrated and described a preferred embodiment of the invention. In the drawing, like reference numerals indicate corresponding parts throughout the several views.

BRIEF DESCRIPTION OF DRAWING

In the drawing,

FIG. 8 is an enlarged view of a sampling needle in longitudinal axial section;

FIG. 9 is a fragmentary view in vertical section taken along the line 9—9 of FIG. 2; and FIG. 10 is a fragmentary view in vertical section taken along the line 10—10 of FIG. 2.

DESCRIPTION OF THE PREFERRED EMBODIMENT

Figure 1:
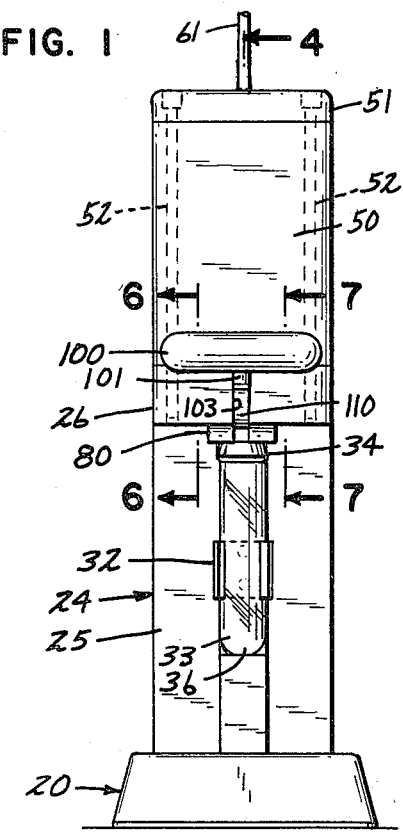
FIG. 1 is a view of the invention in front elevation.
Figure 2:
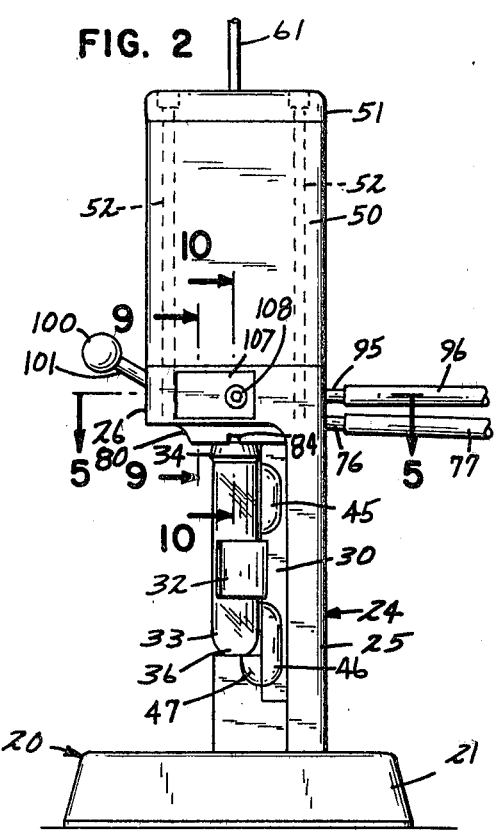
FIG. 2 is a view of the invention in side elevation.
Figure 3:
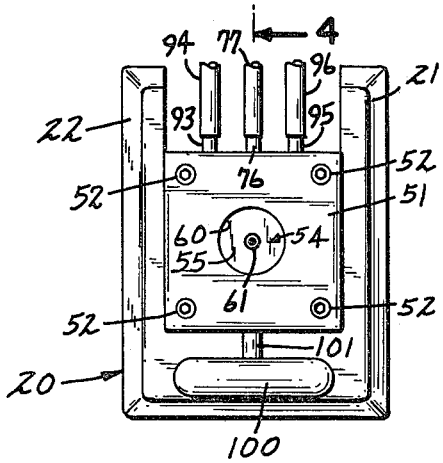
FIG. 3 is a view of the invention in plan.

As shown in the drawing, the invention comprises a base 20 having a pair of rearward arms 21, 22 between which there is secured by a fastener 23, a standard 24 including a vertical leg portion 25 and a horizontal cap portion 26. Centrally secured to leg portion 25 by fasteners 27 is a mounting strip 30 to which there is secured, by fasteners 31, a mounting clip 32 adapted to resiliently receive sample containers and hold them with their axes vertical. One such container is shown at 33, and has a closure or stopper 34 characterized by being capable of axial penetration by a needle, and of sealing itself against the outward passage of the blood 35 contained therein when the penetrating needle is withdrawn. The rounded bottom 36 of container 33 is received in a depression 37 formed in a mounting foot 38 secured in place on base 20 by a detent 40 including a spring 41 and a ball 42 engaging a suitably placed socket 43 in foot 38. A depression 44 like depression 37 is formed in base 20, to receive the rounded bottom of sample tubes of a second, longer size. Strip 30 is provided with finger grooves 45, 46, and foot 38 is provided with grooves 47, to facilitate insertion and removal of sample containers 33.

A casing 50 having a lid 51 is mounted on cap portion 26 by suitable fasteners 52, and is bored along a vertical axis to form the cylinder 53 of a linear fluid motor 54 having a piston 55 moving in cylinder 53 and including sealing rings 56 and 57. Lid 51 has a central aperture 60 through which a flexible tube 61 may pass to connect the apparatus with the hematology analyzer, not shown. Piston 55 is axially bored to mount a transfer needle 62, better shown in FIG. 8 to comprise a solid point 63, an inner tube 64, and an outer tube 65. Inner tube 64 extends upward beyond outer tube 65 through piston 55, to receive flexible tubing 61, both tubes of the needle being secured in piston 55. Tube 65 is mounted on point 63, and tube 64 is mounted in point 63, all three being provided with bores aligned to comprise a single radial passage 66 communicating with the bore 68 of tube 64. Tubes 64, 65 are also configured to seal a longitudinal space 67 coaxially therebetween, and apertures 70 and 71 are formed in outer tube 65 to give access to space 67 at sites selected as will be described below.

Cap portion 26 is axially bored at 73 to pass needle 62, being provided with sealing O-rings 74, and also includes an annular chamber 75 with which there communicates a drain tap 76 extending rearwardly to receive a flexible drain tube 77. Tap 76 is configured to slope slightly downwards, to facilitate drainage of liquid from chamber 75. A contact piece 80 is secured below cap portion 26 by fasteners 81. It includes a further O-ring 82 sealing around needle 62, and is formed with a pair of radial grooves 83, 84 which interrupt its engagement with the top of closure 34, the latter being concave at its top as at 85.

The length of needle 62, the stroke of piston 55 in cylinder 53, and the length of the shortest standard sample container are such that when piston 55 is at its upward extreme of travel point 63 is withdrawn within contact piece 80 and passage 66 is in communication with chamber 75, while when piston 55 is at its downward extreme of travel, point 63 is near the bottom of the shortest standard sample container, aperture 71 opens within the container below stopper 34, and aperture 70 opens in the concavity 85 in the top of closure 34, and is in communication with grooves 83, 84.

Figure 4:
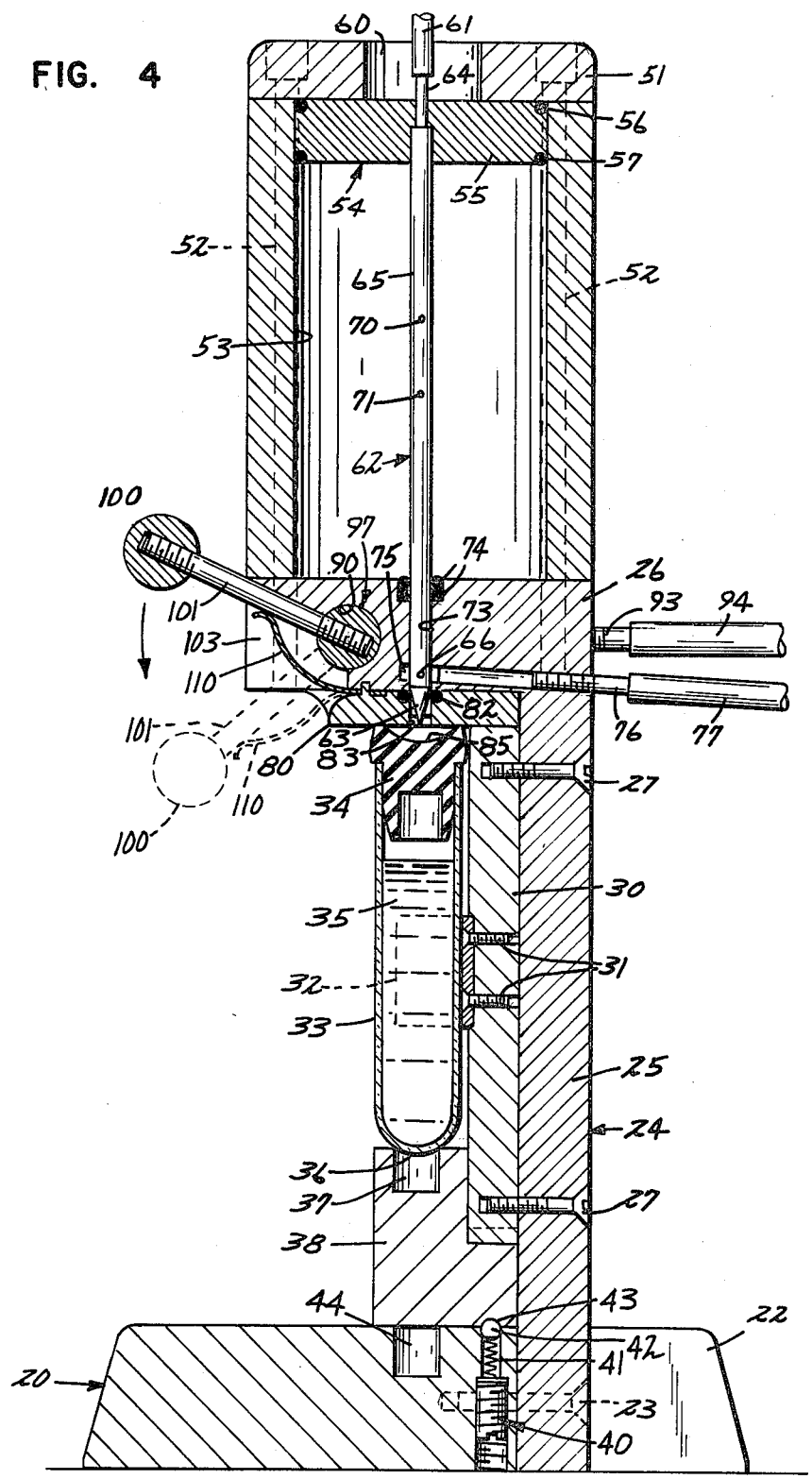
FIG. 4 is a longitudinal sectional view of the invention to a larger scale as seen from the line 4—4 of FIG. 1.
Figure 5:
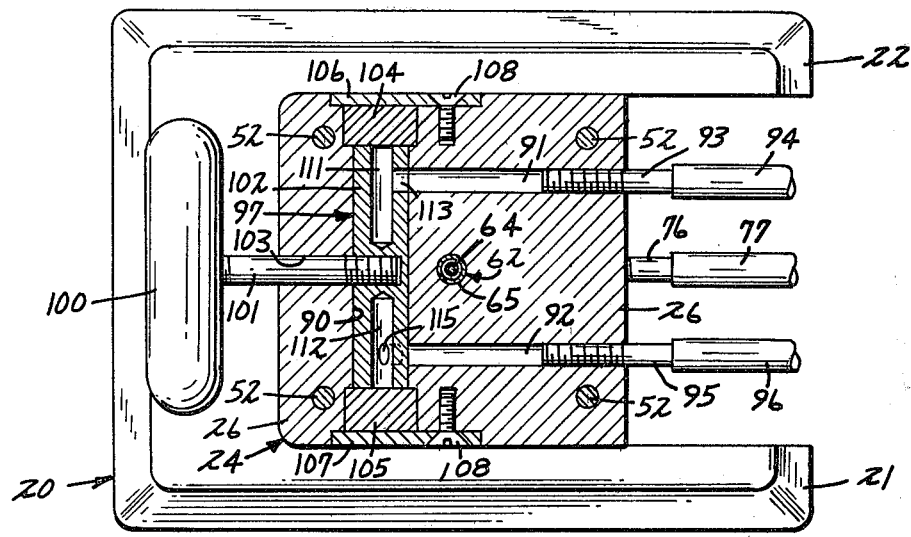
FIG. 5 is a view of the invention in horizontal section taken along the line 5—5 of FIG. 2.

As shown in FIG. 5, cap portion 26 is provided with a transverse bore 90 intersected by a pair of cross bores 91 and 92. Cross bore 91 is connected by a tap 93 with a flexible tube 94 supplied with positive fluid pressure from the hematology analyzer or some other source, and cross bore 92 is connected by a tap 95 with a flexible tube 96 similarly supplied with negative fluid pressure. A rotary plug valve 97 is rotated in bore 90 by a handle 100 having a shaft 101 secured in the body 102 of valve 97, and moving in a slot 103 in cap portion 26. Body 102 is secured in bore 90 by sealing plugs 104 and 105 and clamping plates 106 and 107, secured to cap portion 26 by fasteners 108. A leaf spring 110 is secured between cap portion 26 and contact member 80, and normally urges handle 101 to rotate valve 97 in a clockwise direction as seen in FIG. 4.

Valve body 102 is provided with axial bores 111 and 112 which are closed at their adjacent ends and do not connect with each other. Intersecting bore 111 at right angles, and spaced axially along bore 111, are a pair of cross bores 113 and 114. Intersecting bore 112 at right angles, and spaced along the bore, are another pair of cross bores 115 and 116. Bore 113 is positioned transversely to line up with bore 91, and bore 115 is positioned to line up with bore 92, in certain rotated positions of body 102.

A pair of bore 117 and 118 in member 26 open into bore 90 and into cylinder 53. Bore 114 is positioned to line up with bore 117, and bore 116 with bore 118, in certain rotated positions of body 102.

Figure 6:
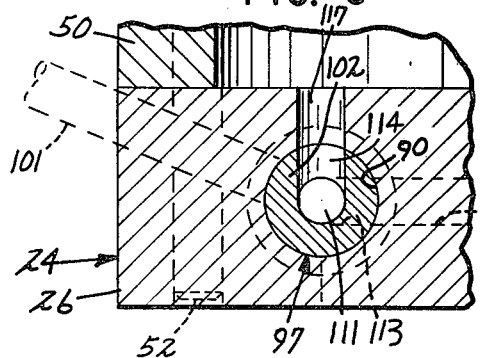
FIG. 6 is a fragmentary view in vertical section taken along the line 6—6 of FIG. 1.
Figure 7:
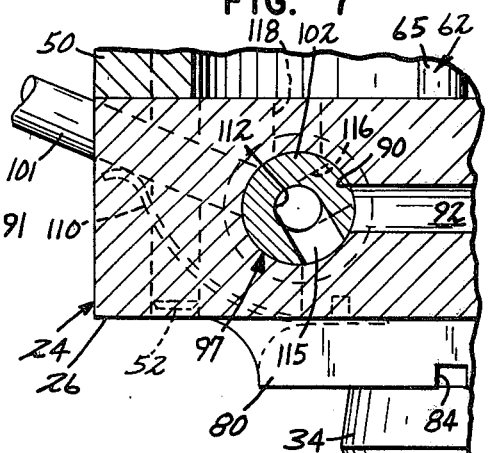
FIG. 7 is a fragmentary view in vertical section taken along the line 7—7 of FIG. 1.

FIGS. 6 and 7 show that when handle 100 is in the "NORMAL" solid line position of FIG. 4, positive pressure fluid is supplied through bores 91, 113, 111, 114, and 117 to cylinder 53, displacing piston 55 to its upper extreme of travel: at the same time, negative pressure fluid is cut off from cylinder 53 because bore 115 is not aligned with bore 92.

Figure 7A:
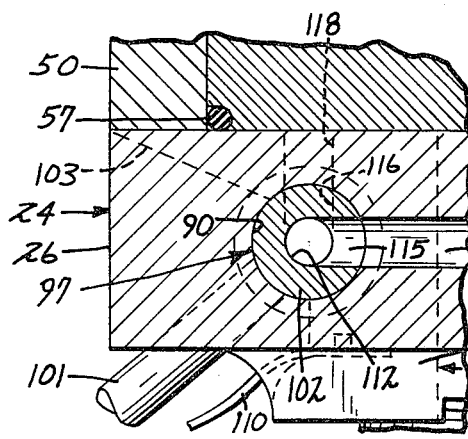
FIG 7A is a view like FIG. 7 showing a different position of the parts.
Figure 6A:
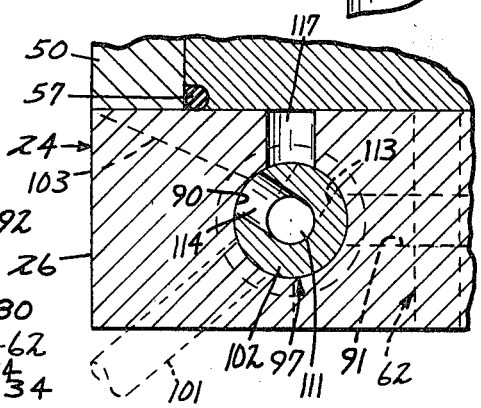
FIG. 6A is a view like FIG. 6 showing a different position of the parts.

FIGS. 6A and 7A show that when handle 100 is in the broken line position of FIG. 4, negative pressure fluid is supplied through bores 92, 115, 112, 116, and 118 to cylinder 53, displacing piston 55 to its lower extreme of travel: at the same time positive pressure fluid is cut off from cylinder 53 because bore 113 is not aligned with bore 91.

OPERATION

In use flexible tube 61 from the sampling connection of the analyzer is connected to inner tube 64 of needle 62 above piston 55, and the analyzer is energized for normal operation. The flexible tubes 94 and 96 are connected from taps 93 and 95 to sources of positive and negative fluid pressures, which may be provided by the analyzer. Flexible tube 77 is connected from tap 76 to a suitable discharge drain. Foot 38 is positioned on or removed from base 20 according to the length of sample containers to be used.

Leaf spring 110 is holding handle 100 in its upward position, so that the bores of valve body 102 are as shown in FIGS. 6 and 7. Negative pressure is cut off from the fluid motor by the rotation of bore 115 out of alignment with bore 92. Positive pressure is supplied from tube 94 through tap 93 and bores 91, 113, 111, 114, and 117, to cylinder 53, and piston 55 is moved to its upward extreme of travel, needle 62 being retracted within contact piece 80 of the fluid motor.

The first sample container is now shaken and inserted in clip 32, its bottom resting in depression 37 (or 44) and its closure 34 engaging contact piece 80. The technician now depresses handle 100, rotating valve body 102 to the position shown in FIGS. 6A and 7A. Positive pressure is now cut off by displacement of bore 113 out of alignment with bore 91. Negative pressure is supplied through bores 92, 115, 112, 116, and 118 to cylinder 53, and ambient air pressure through aperture 60 displaces piston 55 to its lower extreme of travel. This forces needle 62 downward so that point 63 penetrates container closure 34 and moves toward the container bottom, whereby passage 66 is positioned in the blood to be sampled. At the same time, as shown in FIG. 10, aperture 71 opens below closure 34 and aperture 70 opens above the closure, placing space 67 in communication with the atmosphere through grooves 83 and 84. The technician now actuates the analyzer to aspirate blood from the sample container, replacement air flowing through grooves 83 and 84, aperture 70, space 67, and aperture 71 into the container. When the sampling is completed the technician releases handle 100, and spring 110 moves it back to its initial position. Fluid motor operation as described above forces piston 55 upward, withdrawing needle 62 through closure 34 which wipes any fluid off the surface of the needle.

The analyzer then automatically cleanses its inlet parts, cleansing fluid being supplied through flexible tube 61 to pass through the bore of inner tube 64 of needle 62, out through passage 66 into chamber 75, and then through tap 76 and flexible tube 77 to the drain, no contact of even this cleansing liquid with the technician being possible.

The container which has been sampled is now free from needle 62 and may be removed, still closed, for suitable storage or disposition.

From the foregoing it will be apparent that the present invention safeguards medical technicians from hazards, provides automatic movement of the sampling needle into and out of the container, wipes the outside of the needle, retracts the needle to a site where it cannot contact the worker, and provides appropriate disposition of cleansing liquid when the analyzer discharges it.

Numerous characteristics and advantages of the invention have been set forth in the foregoing description, together with details of the structure and function of the invention, and the novel features thereof are pointed out in the appended claims. The disclosure, however, is illustrative only, and changes may be made in detail, especially in matters of shape, size, and arrangement of parts, within the principle of the invention, to the full extent indicated by the broad general meaning of the terms in which the appended claims are expressed.

What is claimed is:

1. The method of extracting a sample from a container of fluid having a longitudinal axis and a penetrable, self-sealing enclosure at one end, comprising the steps of:
   (1) mounting said container with said axis vertical and said closure upward,
   (2) actuating a hollow needle having a plurality interconnected apertures and passageways therein, axially penetrate said closure and enter said container,
   (3) draining contents from said container through needle while simultaneously admitting replacement air to said container,
   (4) withdrawing said needle from said container into a substantially enclosed area while wiping any contents from the surface of said needle as it is being withdrawn,
   (5) passing a cleaning liquid through a portion of said apertures and passageways of said hollow needle while preventing said cleaning liquid from having any contact with said container, and
   (6) removing said cleaning fluid from said needle without exposing said fluid to the ambient atmosphere surrounding said container and said needle.

2. A hollow needle having a generally central bore extending along a longitudinal axis;
   means mounting said needle for linear movement along said axis;
   reversible fluid motor means for causing said linear movement of said needle between first and second positions along said axis;
   valve means operable to reversibly actuate said fluid motor means;
   means for mounting a container of liquid, having a penetrable self-sealing closure, on said axis for penetration when said needle moves into said first position;
   means actuable to withdraw contents from said container through said needle bore;
   means within said needle independent of said bore for affording ingress of ambient air to said container to replace the contents withdrawn; and means effective when said needle is moved into said second position for containing and discharging a cleaning liquid emitted through said needle bore and preventing exposure of the cleaning liquid to the ambient atmosphere surrounding said structure.

3. A sampling apparatus comprising:
   a generally upright frame structure;
   a power source;
   a hollow sampling needle positioned within said frame structure;
   a container having a longitudinal axis and closure means for sealing said container from outward passage of contents contained therein, said closure means being constructed and arranged for axial penetration by said needle;
   means on said frame structure for resiliently holding said container;
   means, connecting said needle with said power source, for alternately moving said needle into a first position within said container and a second position outside said container;
   a chamber within said frame structure including means for sealing said chamber from exposure with the ambient atmosphere;
   means for aspirating contents from said container when said needle is in said first position and for delivering a cleansing fluid to said needle when said needle is in said second position;
   said needle having a predetermined length, a bore, a solid point and a radial passage near said point communicating with said bore, said bore being in fluid communication with said aspirating and delivering means, said needle including a space coaxially therein and in addition to said bore, a first outward aperture and a second outward aperture, each of said apertures communicating with said space at separate locations along the length of said needle, said apertures being positioned so that when said needle is in said first position said first outward aperture and said radial passage are positioned within said container with said second outward aperture positioned outside said container, and when said needle is in said second position said radial passage is contained in said sealed chamber.

4. A sampling apparatus comprising:

a frame structure;

a hollow sampling needle having a bore extending along a longitudinal axis;

means for mounting said needle in said frame structure for linear movement along said axis;

reversible fluid motor means for causing said linear movement of said needle between a first position and a second position along said axis;

valve means operable for reversibly actuating said fluid motor means;

a container having a longitudinal axis and closure means for sealing said container from outward passage of contents contained therein, said closure means being constructed and arranged for axial penetration by said needle;

means for mounting said container in said frame structure for penetration when said needle is moved into said first position;

means actuable to withdraw contents from said container through said needle bore, including a radial passage in said needle communicating with said bore;

said needle including a space coaxially therein independent of said bore, a first outward aperture and a second outward aperture, said apertures being spaced apart along the axis of said needle for affording ingress of ambient air into said container to replace the contents withdrawn therefrom;

means effective when said needle is moved into said second position for containing and discharging a cleaning liquid emitted through said needle bore for cleaning said needle;

and means including a sealed chamber within said frame structure for preventing exposure of said cleaning liquid to the ambient atmosphere surrounding said structure.

* * * * *

UNITED STATES PATENT AND TRADEMARK OFFICE
CERTIFICATE OF CORRECTION

PATENT NO. : 4,342,341
DATED : August 3, 1982
INVENTOR(S) : Peter F. Lee

It is certified that error appears in the above—identified patent and that said Letters Patent is hereby corrected as shown below:

Column 4, line 32, "bore" should be --bores--.

Claim 1, Column 5, line 66, after "plurality" and before "inter" insert --of--.

Claim 1, Column 5, line 68, after "ally" and before "penetrate" insert --to--.

Claim 1, Column 6, line 1, after "through" insert --said--.

Signed and Sealed this

Sixteenth Day of November 1982

[SEAL]

Attest:

GERALD J. MOSSINGHOFF

Attesting Officer  Commissioner of Patents and Trademarks